United States Patent
Corbin et al.

(10) Patent No.: US 10,327,807 B2
(45) Date of Patent: *Jun. 25, 2019

(54) ENDOSCOPIC SURGICAL SYSTEMS AND METHODS

(71) Applicant: Stryker European Holdings I, LLC, Kalamazoo, MI (US)

(72) Inventors: Erika Corbin, Mahwah, NJ (US); Lori Dombrowski, Elmwood Park, NJ (US); David Talijan, Mahwah, NJ (US); Felix Eugenio Plaud Pagan, Mahwah, NJ (US)

(73) Assignee: Stryker European Holdings I, LLC, Kalamazoo, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/966,699

(22) Filed: Apr. 30, 2018

(65) Prior Publication Data

US 2018/0243002 A1  Aug. 30, 2018

Related U.S. Application Data

(63) Continuation of application No. 15/704,489, filed on Sep. 14, 2017, now Pat. No. 9,980,744, which is a
(Continued)

(51) Int. Cl.
*A61B 1/32* (2006.01)
*A61B 17/34* (2006.01)
(Continued)

(52) U.S. Cl.
CPC ...... *A61B 17/3421* (2013.01); *A61B 17/0293* (2013.01); *A61B 17/3439* (2013.01);
(Continued)

(58) Field of Classification Search
CPC combination set(s) only.
See application file for complete search history.

(56) References Cited

U.S. PATENT DOCUMENTS

| 2,821,190 A | 1/1958 | Chase |
| 4,538,594 A | 9/1985 | Boebel et al. |

(Continued)

FOREIGN PATENT DOCUMENTS

| EP | 1192905 A1 | 4/2002 |
| WO | 9734536 A2 | 9/1997 |

(Continued)

OTHER PUBLICATIONS

Ditsworth, "Endoscopic Transforaminal Lumbar Discectomy and Reconfiguration: A Posterolateral Approach into the Spinal Canal", Endoscopy, 1998; 49, 588-598.

(Continued)

*Primary Examiner* — Sameh R Boles
(74) *Attorney, Agent, or Firm* — Lerner, David, Littenberg, Krumholz & Mentlik, LLP

(57) ABSTRACT

An access system is provided for establishing an access path to a surgical site within a patient. The access system comprises an access portal defining a working channel with a central axis, and an adaptor with a mating section mountable to the access portal. The adaptor is selectively rotatable about the central axis. The access portal includes a plurality of openings and the adaptor includes a plurality of projections, each of the projections and openings being arranged so that, in a first orientation, the openings and projections align to allow mounting of the adaptor to the access portal and, in a second orientation, the openings and projections do not align to prevent disassociation between the adaptor and the access portal. The adaptor also includes a holder for a viewing device, the viewing device being movable with the
(Continued)

adaptor about the access portal and vertically translatable relative to the access portal.

14 Claims, 6 Drawing Sheets

Related U.S. Application Data continuation of application No. 14/640,608, filed on Mar. 6, 2015, now Pat. No. 9,788,856.

(60) Provisional application No. 61/951,183, filed on Mar. 11, 2014.

(51) Int. Cl.
*A61B 17/02* (2006.01)
*A61B 1/317* (2006.01)
*A61B 17/00* (2006.01)
*A61B 90/50* (2016.01)

(52) U.S. Cl.
CPC ............... *A61B 1/317* (2013.01); *A61B 90/50* (2016.02); *A61B 2017/00477* (2013.01)

(56) References Cited

U.S. PATENT DOCUMENTS

| | | |
|---|---|---|
| 4,550,715 A | 11/1985 | Santangelo et al. |
| 4,610,242 A | 9/1986 | Santangelo et al. |
| 4,686,965 A | 8/1987 | Bonnet et al. |
| 4,807,593 A | 2/1989 | Ito |
| 5,071,410 A | 12/1991 | Pazell |
| 5,313,962 A | 5/1994 | Obenchain |
| 5,351,678 A | 10/1994 | Clayton et al. |
| 5,396,880 A | 3/1995 | Kagan et al. |
| 5,472,426 A | 12/1995 | Bonati et al. |
| 5,486,155 A | 1/1996 | Muller et al. |
| 5,540,648 A | 7/1996 | Yoon |
| 5,540,649 A | 7/1996 | Bonnell et al. |
| 5,551,946 A | 9/1996 | Bullard |
| 5,586,968 A | 12/1996 | Grundl et al. |
| 5,645,519 A | 7/1997 | Lee et al. |
| 5,762,604 A | 6/1998 | Kieturakis |
| 5,779,623 A | 7/1998 | Bonnell |
| 5,792,044 A | 8/1998 | Foley et al. |
| 5,810,712 A | 9/1998 | Dunn |
| 5,817,013 A | 10/1998 | Ginn et al. |
| 5,865,802 A | 2/1999 | Yoon et al. |
| 5,902,231 A | 5/1999 | Foley et al. |
| 5,954,635 A | 9/1999 | Foley et al. |
| 5,976,146 A | 11/1999 | Ogawa et al. |
| 6,083,151 A | 7/2000 | Renner et al. |
| 6,129,661 A | 10/2000 | Iafrati et al. |
| 6,142,931 A | 11/2000 | Kaji |
| 6,152,871 A | 11/2000 | Foley et al. |
| 6,162,170 A | 12/2000 | Foley et al. |
| 6,176,823 B1 | 1/2001 | Foley et al. |
| 6,187,000 B1 | 2/2001 | Davison et al. |
| 6,206,822 B1 | 3/2001 | Foley et al. |
| 6,217,509 B1 | 4/2001 | Foley et al. |
| 6,361,488 B1 | 3/2002 | Davison et al. |
| 6,371,968 B1 | 4/2002 | Kogasaka et al. |
| 6,458,077 B1 | 10/2002 | Boebel et al. |
| 6,520,907 B1 | 2/2003 | Foley et al. |
| 6,530,880 B2 | 3/2003 | Pagliuca |
| 6,530,926 B1 | 3/2003 | Davison |
| 6,575,899 B1 | 6/2003 | Foley et al. |
| 6,605,036 B1 | 8/2003 | Wild |
| 6,652,553 B2 | 11/2003 | Davison et al. |
| 6,679,833 B2 | 1/2004 | Smith et al. |
| 6,758,853 B2 | 7/2004 | Kieturakis et al. |
| 6,800,084 B2 | 10/2004 | Davison et al. |
| 6,811,558 B2 | 11/2004 | Davison et al. |
| 6,821,243 B2 | 11/2004 | Pagliuca et al. |
| 6,837,891 B2 | 1/2005 | Davison et al. |
| 6,851,430 B2 | 2/2005 | Tsou |
| 6,890,295 B2 | 5/2005 | Michels et al. |
| 6,962,563 B2 | 11/2005 | Yasunaga |
| 7,001,397 B2 | 2/2006 | Davison et al. |
| 7,033,369 B2 | 4/2006 | Davison et al. |
| 7,056,321 B2 | 6/2006 | Pagliuca et al. |
| 7,108,705 B2 | 9/2006 | Davison et al. |
| 7,144,393 B2 | 12/2006 | DiPoto et al. |
| 7,198,598 B2 | 4/2007 | Smith et al. |
| 7,223,278 B2 | 5/2007 | Davison et al. |
| 7,226,451 B2 | 6/2007 | Shluzas et al. |
| 7,320,688 B2 | 1/2008 | Foley et al. |
| 7,427,264 B2 | 9/2008 | Nowitzke et al. |
| 7,431,693 B2 | 10/2008 | Pagliuca et al. |
| 7,641,670 B2 | 1/2010 | Davison et al. |
| 7,651,496 B2 | 1/2010 | Keegan et al. |
| 7,670,354 B2 | 3/2010 | Davison et al. |
| 7,674,273 B2 | 3/2010 | Davison et al. |
| 7,682,370 B2 | 3/2010 | Pagliuca et al. |
| 7,691,120 B2 | 4/2010 | Shluzas et al. |
| 7,699,877 B2 | 4/2010 | Davison |
| 7,722,530 B2 | 5/2010 | Davison |
| 7,731,737 B2 | 6/2010 | DiPoto |
| 7,766,930 B2 | 8/2010 | DiPoto et al. |
| 7,799,036 B2 | 9/2010 | Davison et al. |
| 7,824,410 B2 | 11/2010 | Simonson et al. |
| 7,850,695 B2 | 12/2010 | Pagliuca et al. |
| 7,892,171 B2 | 2/2011 | Davison et al. |
| 7,892,249 B2 | 2/2011 | Davison et al. |
| 7,976,464 B2 | 7/2011 | Shluzas et al. |
| 7,985,237 B2 | 7/2011 | Davison et al. |
| 7,985,247 B2 | 7/2011 | Shluzas et al. |
| 7,993,378 B2 | 8/2011 | Foley et al. |
| 8,007,492 B2 | 8/2011 | DiPoto et al. |
| 8,088,139 B2 | 1/2012 | Scopton et al. |
| 8,142,448 B2 | 3/2012 | Pasricha et al. |
| 8,251,997 B2 | 8/2012 | Michelson |
| 8,277,486 B2 | 10/2012 | Davison |
| 8,317,817 B2 | 11/2012 | Davison et al. |
| 8,414,475 B2 | 4/2013 | Sholev |
| 9,320,610 B2 | 4/2016 | Alheidt et al. |
| 2002/0022764 A1 | 2/2002 | Smith et al. |
| 2002/0111534 A1 | 8/2002 | Suzuki et al. |
| 2003/0073998 A1 | 4/2003 | Pagliuca et al. |
| 2003/0139648 A1 | 7/2003 | Foley et al. |
| 2003/0195549 A1 | 10/2003 | Davison et al. |
| 2003/0195550 A1 | 10/2003 | Davison et al. |
| 2003/0195551 A1 | 10/2003 | Davison et al. |
| 2004/0093002 A1 | 5/2004 | Davison et al. |
| 2004/0098012 A1 | 5/2004 | Davison et al. |
| 2004/0102804 A1 | 5/2004 | Chin |
| 2004/0133201 A1 | 7/2004 | Shluzas et al. |
| 2004/0176763 A1 | 9/2004 | Foley et al. |
| 2004/0186346 A1* | 9/2004 | Smith ............... A61B 17/3417 600/102 |
| 2004/0236317 A1 | 11/2004 | Davison |
| 2005/0021030 A1 | 1/2005 | Pagliuca et al. |
| 2005/0033297 A1 | 2/2005 | Davison |
| 2005/0043754 A1 | 2/2005 | Davison et al. |
| 2005/0075540 A1 | 4/2005 | Shluzas et al. |
| 2005/0085692 A1 | 4/2005 | Kiehn et al. |
| 2005/0090822 A1 | 4/2005 | DiPoto |
| 2005/0113833 A1 | 5/2005 | Davison |
| 2005/0149035 A1 | 7/2005 | Pimenta et al. |
| 2005/0149106 A1 | 7/2005 | DiPoto et al. |
| 2005/0171551 A1 | 8/2005 | Sukovich et al. |
| 2005/0222495 A1 | 10/2005 | Okada et al. |
| 2005/0240209 A1 | 10/2005 | Hamada |
| 2005/0251192 A1 | 11/2005 | Shluzas et al. |
| 2005/0273131 A1 | 12/2005 | Shluzas et al. |
| 2005/0273132 A1 | 12/2005 | Shluzas et al. |
| 2005/0273133 A1 | 12/2005 | Shluzas et al. |
| 2006/0030850 A1 | 2/2006 | Keegan et al. |
| 2006/0052812 A1 | 3/2006 | Winer |
| 2006/0069404 A1 | 3/2006 | Shluzas et al. |
| 2006/0089662 A1 | 4/2006 | Davison et al. |
| 2006/0264999 A1 | 11/2006 | Davison et al. |
| 2006/0271057 A1 | 11/2006 | Shluzas et al. |

(56) References Cited

U.S. PATENT DOCUMENTS

| | | |
|---|---|---|
| 2006/0276821 A1 | 12/2006 | Davison et al. |
| 2006/0276822 A1 | 12/2006 | Davison et al. |
| 2006/0293678 A1 | 12/2006 | Davison et al. |
| 2007/0142857 A1 | 6/2007 | Dipoto et al. |
| 2007/0265497 A1 | 11/2007 | Brown et al. |
| 2007/0299387 A1 | 12/2007 | Williams et al. |
| 2008/0221628 A1 | 9/2008 | Milbocker et al. |
| 2009/0048622 A1 | 2/2009 | Wilson |
| 2010/0185054 A1 | 7/2010 | Ramzipoor et al. |
| 2010/0331620 A1* | 12/2010 | Sohn ................. A61B 1/00006 600/104 |
| 2013/0066159 A1 | 3/2013 | Pagliuca et al. |
| 2013/0066160 A1 | 3/2013 | Davison et al. |
| 2014/0257486 A1 | 9/2014 | Alheidt |

FOREIGN PATENT DOCUMENTS

| | | |
|---|---|---|
| WO | 0018306 A1 | 4/2000 |
| WO | 2002009801 A1 | 2/2002 |

OTHER PUBLICATIONS

Partial European Search Report for Application No. EP 15158560 dated Mar. 22, 2016.
Spine, "Our Technology You Skill", SOPRO COMEG, copyright 2006.
Stryker Spine, AVS TL PEEK Spacer System, Surgical Technique, 2005.

* cited by examiner

FIG. 2A  FIG. 2B

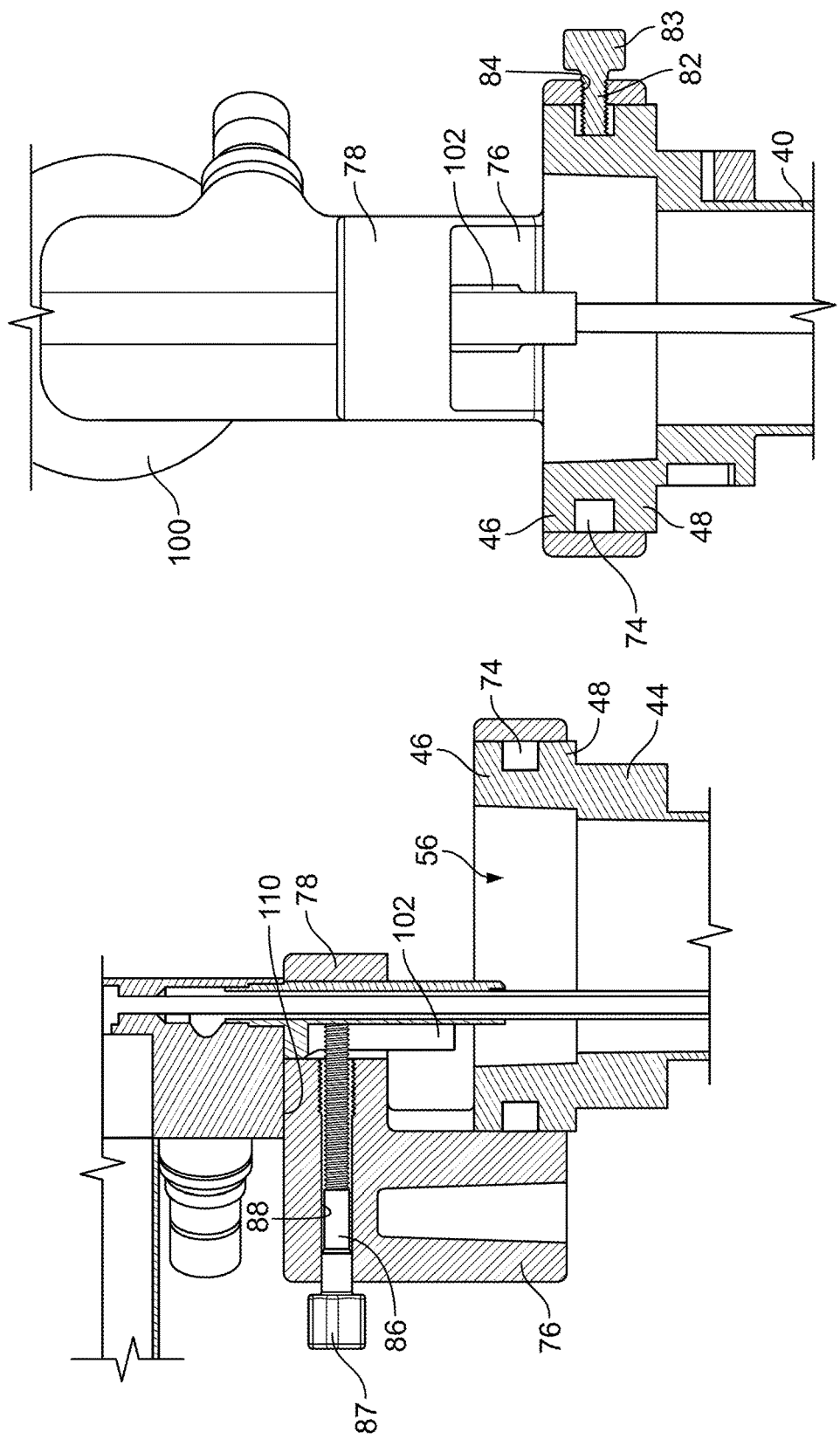

ENDOSCOPIC SURGICAL SYSTEMS AND METHODS

CROSS-REFERENCE TO RELATED APPLICATIONS

This application is a continuation of U.S. patent application Ser. No. 15/704,489, filed on Sep. 14, 2017, which is a continuation of U.S. patent application Ser. No. 14/640,608, filed on Mar. 6, 2015, which claims the benefit of the filing date of U.S. Provisional Application No. 61/951,183, filed Mar. 11, 2014, the disclosures of which are hereby incorporated by reference herein.

BACKGROUND OF THE INVENTION

The present invention relates to endoscopic surgical systems and methods, and particularly to minimally-invasive access systems used with endoscopic tools and viewing devices to conduct surgical procedures on a patient (for instance, on the patient's spine).

Common degenerative spinal diseases, such as chronic degeneration of an intervertebral disc of the spine, may result in substantial pain and discomfort for a patient. Frequently, diseases of this type need to be treated through surgical intervention, which may include replacing the affected disc(s) and potentially fusing the associated vertebrae through the use of an implant or other like device. In particular applications, adjacent vertebral bodies may be fused via an implant, through screw arrangements, and/or by using bone graft material to secure the vertebrae in a fixed state. Exemplary indications for such devices include, but are not limited to, spinal stenosis, degenerative disc disease with a loss of disc height, disc herniation, spondylolisthesis, retrolisthesis, and discogenic back pain.

In replacing a diseased intervertebral disc(s) and effecting fusion, it is necessary to gain access to the disc space to conduct the surgical procedure. Increasingly, access is provided in a minimally-invasive manner, such as through expandable or non-expandable access portals (e.g., retractors or cannula, which provide access to the disc space through the skin and tissue of the patient). The benefits of a minimally-invasive procedure include, for example, less trauma to the patient, as well as improved procedure and recovery times. In conducting a minimally-invasive surgical procedure, however, it is important for the surgeon to maintain good visualization of the working area (e.g., the space within the patient where the surgeon is performing the procedure). Endoscopic tools and devices have been developed for use with minimally-invasive access portals to allow visualization of the working area. As an example, a surgeon might have the option of conducting a minimally-invasive procedure through a retractor or a cannula, while viewing the procedure via an endoscope inserted through the retractor or cannula. In this way, the surgeon is able to visualize the working area (e.g., the intervertebral disc(s)) so that the operation can be performed with more precision and confidence.

Although endoscopic devices and methods have been developed to enable a surgeon to conduct minimally-invasive or other surgical procedures with improved visualization of the working area, such endoscopic devices are frequently difficult and/or cumbersome to use. Improvements upon such devices and methods are therefore needed.

BRIEF SUMMARY OF THE INVENTION

A first aspect of the present invention includes an access system for providing an access path to a surgical site within a patient. The access system comprises an access portal defining a working channel with a central axis, the access portal having at least one opening, and an adaptor with a mating section mountable to the access portal, such that the adaptor is selectively rotatable about the central axis, the adaptor having at least one projection movable through the at least one opening in the access portal to mate the adaptor to the access portal, wherein the adaptor includes a holder for holding a viewing device. In some embodiments of this first aspect, the holder extends proximally above a proximal end of the access portal and includes a first aperture with an axis that is aligned with the working channel of the access portal, the first aperture being configured to receive a mounting portion of the viewing device. In other embodiments, the access portal includes first and second flanges spaced apart from one another to define a channel, the first flange including the at least one opening in the access portal.

A second aspect of the invention comprises an access system for providing an access path to a surgical site within a patient, the system comprising an access portal defining a working channel with a central axis, and an adaptor with a mating section mountable to the access portal, such that the adaptor is selectively rotatable about the central axis, wherein the access portal includes a plurality of openings and the adaptor includes a plurality of projections, each of the projections and openings being arranged so that, in a first orientation, the openings and projections align with one another to allow mounting of the adaptor to the access portal and, in a second orientation, the openings and projections do not align to prevent disassociation between the adaptor and the access portal, the adaptor including a holder for holding a viewing device. In an embodiment of this second aspect, when the openings of the access portal and the projections of the adaptor are aligned, in the first orientation, each projection is movable through a respective one of the plurality of openings. In another embodiment, the access portal includes a first flange and the projections of the adaptor are arrangeable under the first flange after being moved through the openings of the access portal.

A third aspect of the invention includes an access system for providing an access path to a surgical site within a patient, the system comprising an access portal defining a working channel with a central axis, and an adaptor with a mating section mountable to the access portal, such that the adaptor is selectively rotatable about the central axis, wherein the access portal includes at least one opening and the adaptor includes at least one projection, the at least one projection and opening being arranged so that, in a first orientation, the opening and projection align with one another and, in a second orientation, the opening and projection do not align, the adaptor including a holder for holding a viewing device. The holder may extend proximally above the proximal end of the access portal in this third aspect, and include a first aperture with an axis that is aligned with the working channel of the access portal, the first aperture being configured to receive a mounting portion of the viewing device. In some cases, the mounting portion of the viewing device is not rotatable within the first aperture.

BRIEF DESCRIPTION OF THE DRAWINGS

A more complete appreciation of the subject matter of the present invention(s) and of the various advantages thereof can be realized by reference to the following detailed description in which reference is made to the accompanying drawings in which:

FIG. 2A is a top perspective view of the access portal used in the system of FIGS. 1A-B.

FIG. 2B is a top perspective view of an adaptor used to mount an endoscopic viewing device to the access portal of FIG. 2A.

FIGS. 4B-C are cross-sectional views of the access portal, endoscopic viewing device, and adaptor shown in FIG. 4A.

DETAILED DESCRIPTION

In describing the preferred embodiments of the invention (s) illustrated and to be described with respect to the drawings, specific terminology will be used for the sake of clarity. However, the invention(s) is not intended to be limited to any specific terms used herein, and it is to be understood that each specific term includes all technical equivalents, which operate in a similar manner to accomplish a similar purpose.

Figure 1A:
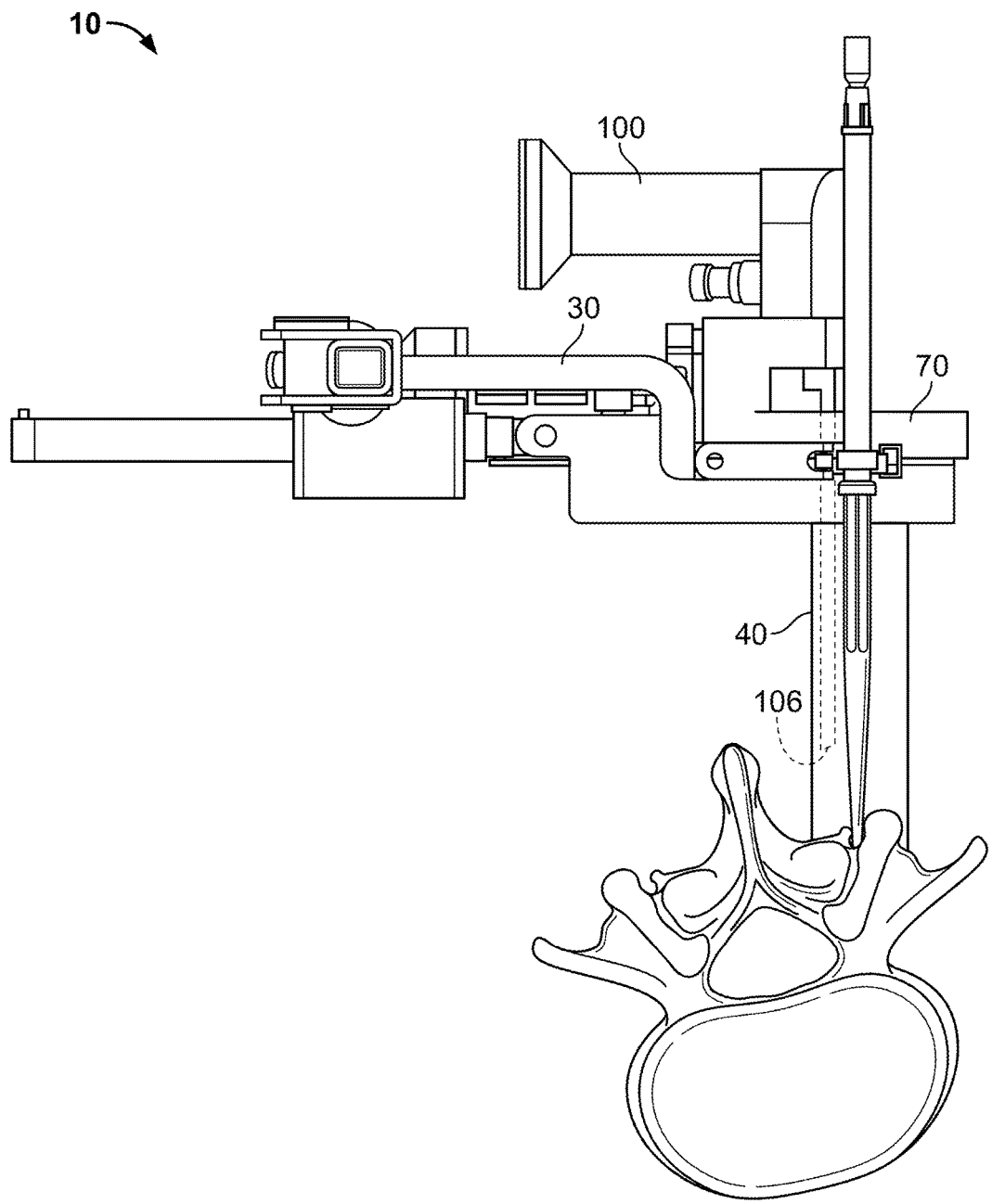
FIG. 1A is a side view of an endoscopic access system according to one embodiment of the present invention.
Figure 1B:
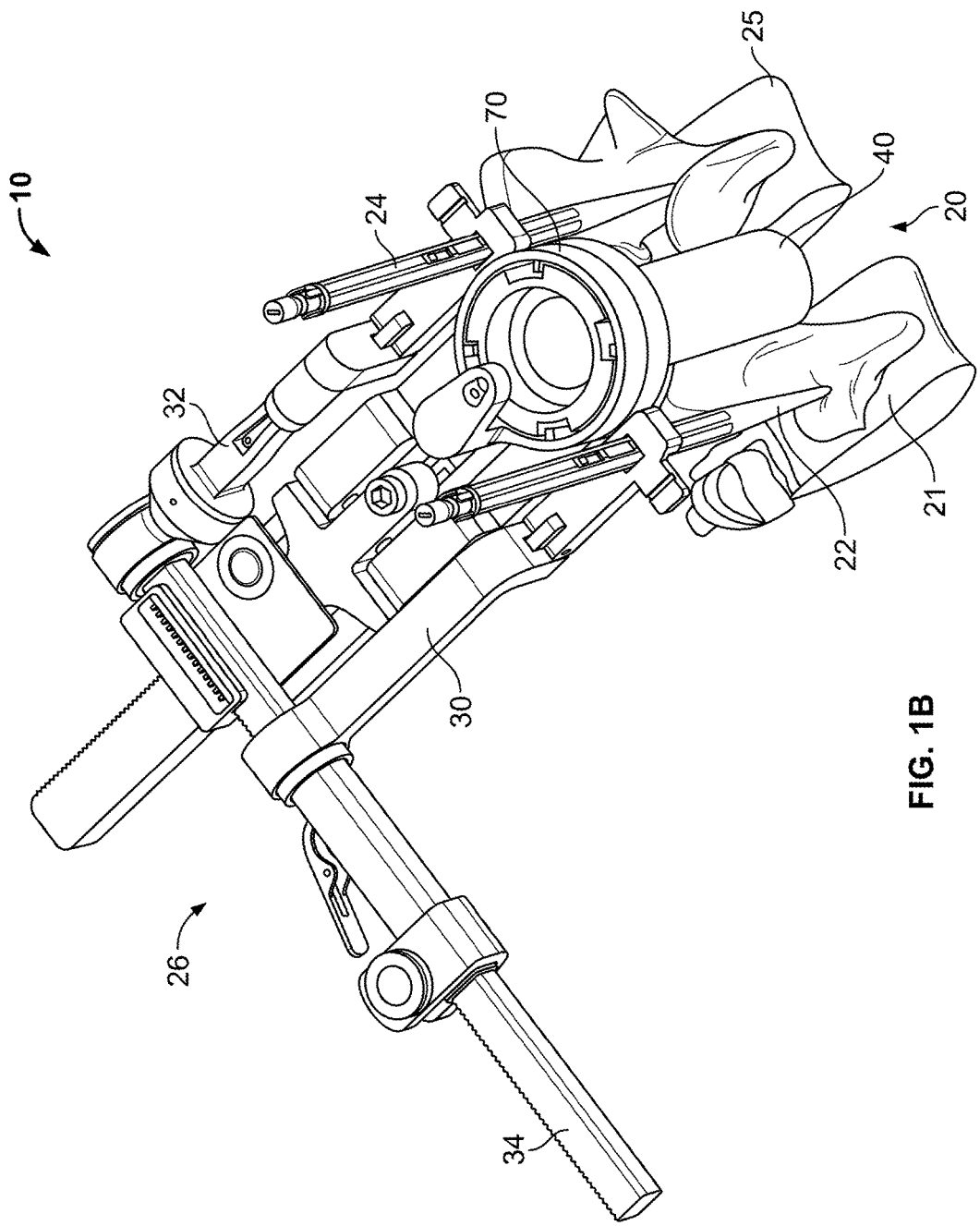
FIG. 1B is a top perspective view of FIG. 1A without the endoscopic viewing device shown.

Referring to FIGS. 1A-B, an exemplary access system 10 is shown. Access system 10 is shown as a pedicle-based retraction system. Although access system 10 is depicted in the context of a pedicle-based retraction system, the methods and devices set forth herein could, of course, be used with many different types of access systems, including those that do not anchor to bone. Such alternate systems are described in more detail below.

Access system 10 is an endoscopic system that includes an access portal 40, in this case a cannula, an adaptor 70 attached to access portal 40, and an endoscopic viewing device 100 mounted to adaptor 70 for viewing a surgical procedure conducted within or through access portal 40. A surgeon can utilize access system 10 to more easily gain a clear image of the working area for a surgical procedure such as, for example, a working area adjacent the spine of a patient. In the case of FIGS. 1A-B, the working area is an intervertebral disc space 20 between adjacent vertebrae 21, 25. Access system 10 therefore provides a multitude of benefits to surgeons, due at least to its improved functionality and ease of use, as set forth in detail below.

Access system 10 includes a frame 26 attached to separate arms 30, 32 (while only two arms 30, 32 are shown, more than two arms can be utilized). A portion of frame 26 includes a bar 34. Arms 30, 32 extend from bar 34 and at least arm 30 (and optionally both arms 30, 32) is movable along bar 34. Arm 30 can be fixed in any location relative to bar 34. Anchoring pins 22, 24 are attached to an end of arms 30, 32 via a clamp mechanism or through other means, and are vertically slidable within the clamp. While arm 32 is fixed relative to bar 34, in one embodiment, it may be rotated about its long axis to rotate the orientation of pin 24.

A clamp is also provided with access system 10 for connecting to access portal 40 to maintain portal 40 in a stable position inside a patient. The clamp can engage access portal 40 and, in one embodiment, is movable along with access portal 40 relative to access system 10. Indeed, access portal 40 may be moved relative to access system 10 in a lateral direction, or towards and away from access system 10. Thus, access system 10 is dynamic in that it allows for movement of anchoring pins 22, 24 via their connected arms 30, 32 and/or movement of access portal 40 by way of its clamp and associated structures.

Access portal 40 is shown in detail in FIG. 2A. In some embodiments, access portal 40 is a cylindrical cannula, although it may be any other shape, such as triangular, trapezoidal, hexagonal, or diamond shaped. It is also contemplated that access portal 40 may be an expandable structure (e.g., a retractor with movable blades or an expandable cannula) or a cannula with a fixed dimension that is tapered in a direction extending towards its distal end or in a direction extending towards its proximal end (e.g., conical). Access portal 40 is capable of providing a minimally-invasive working channel 56 through the skin and tissue of a patient and, in one embodiment, it includes distal and proximal sections 42, 44 that are tubular in shape. Distal and proximal sections 42, 44 of access portal 40 cooperate together to define the extent of working channel 56. In the depicted embodiment, there is a step 45 on an inner surface of access portal 40 at the intersection of distal and proximal sections 42, 44, such that working channel 56 is larger at proximal section 44 as compared to distal section 42. As reflected in FIGS. 3A-B, in some cases working channel 56 may be oval, but in other cases working channel 56 may be circular or any other shape that facilitates access to the surgical site within the patient. An oval shape provides a greater working volume along its major diameter as compared to a circular shape, thus allowing the surgeon more room to work with along an axis coinciding with the major diameter.

Figure 2C:
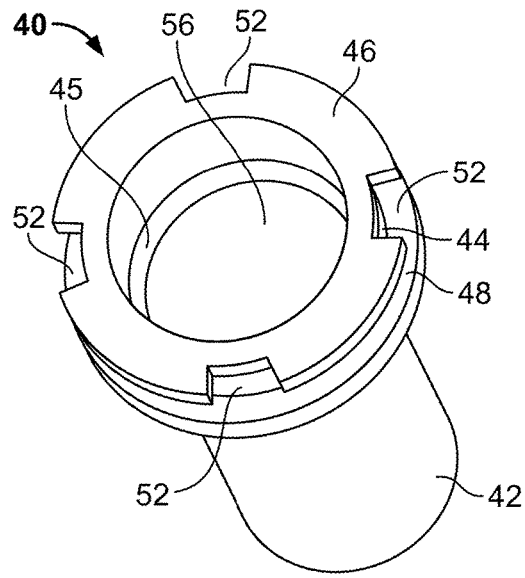
FIG. 2C is a side view showing the adaptor of FIG. 2B being inserted onto the access portal of FIG. 2A.
Figure 2C:
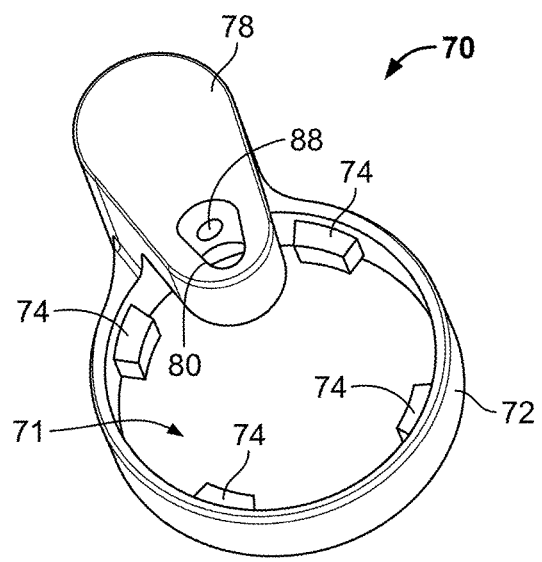
Figure 2C:
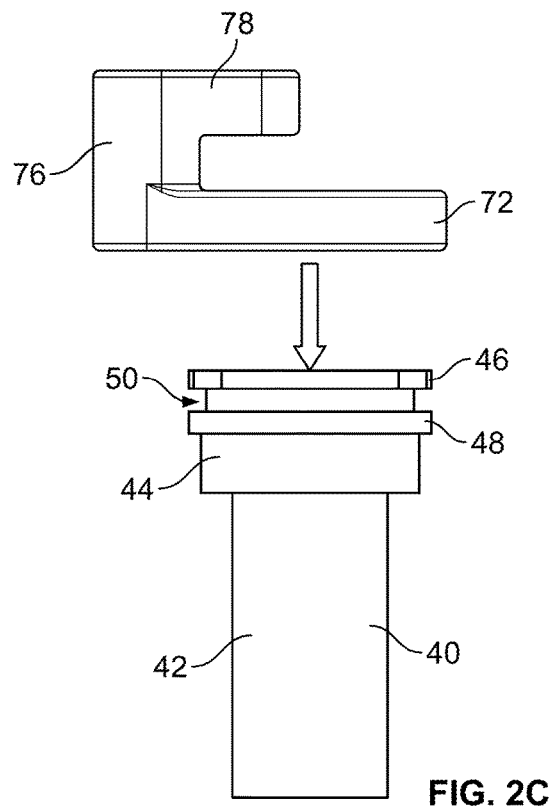

Referring still to FIG. 2A, proximal section 44 of access portal 40 also includes structure for engaging with an adaptor 70 that houses an endoscopic viewing device 100. In a particular embodiment, the structure comprises first and second flanges 46, 48 extending from proximal section 44 of access portal 40, with the first flange 46 having a series of spaced-apart openings 52. Flanges 46, 48 extend circumferentially about proximal section 44 of access portal 40 and define a channel 50 for mating with a portion of adaptor 70, as shown in FIG. 2C. Flange 48 of access portal 40 does not include spaced-apart openings and rather is continuous or substantially continuous about proximal section 44 of portal 40.

Adaptor 70 is shown in FIG. 2B and includes a mating section 72 that, in one embodiment, is circular and defines an opening 71. Mating section 72 may also be semi-circular or any shape that can accommodate or attach with proximal section 44 of access portal 40. Extending inward from mating section 72 are a number of projections 74 that are sized to pass through spaced-apart openings 52 of flange 46 of access portal 40. In particular, the diameter of mating section 72 of adaptor 70 may be roughly equal to or slightly greater than the diameter of flange 46 of access portal 40, and projections 74 of mating section 72 may extend inwardly so as to be slidable through spaced-apart openings 52 of flange 46 of access portal 40. However, projections 74 and/or the diameter of mating section 72 of adaptor 70 may be sized so that neither can travel past flange 48 of access portal 40 (e.g., because the diameter of flange 48 is larger than that of mating section 72 and/or an opening through adaptor 70 defined by projections 74). For instance, due to the inwardly-projecting nature of projections 74, adaptor 70 may not be able to travel past flange 48 of access portal 40 (e.g., due to interference between projections 74 and flange 48). In one embodiment, four (4) projections 74 are present on mating section 72 of adaptor 70, although more or less projections 74 are contemplated.

Figure 3A:
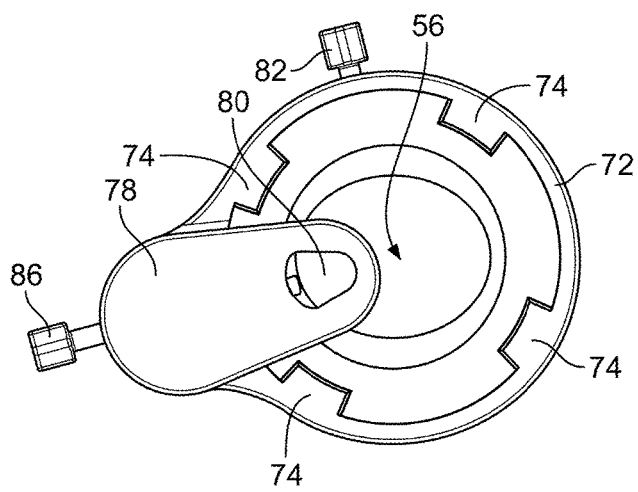
FIGS. 3A-B are top views showing the adaptor of FIG. 2B being rotated to engage the access portal of FIG. 2A.
Figure 3B:
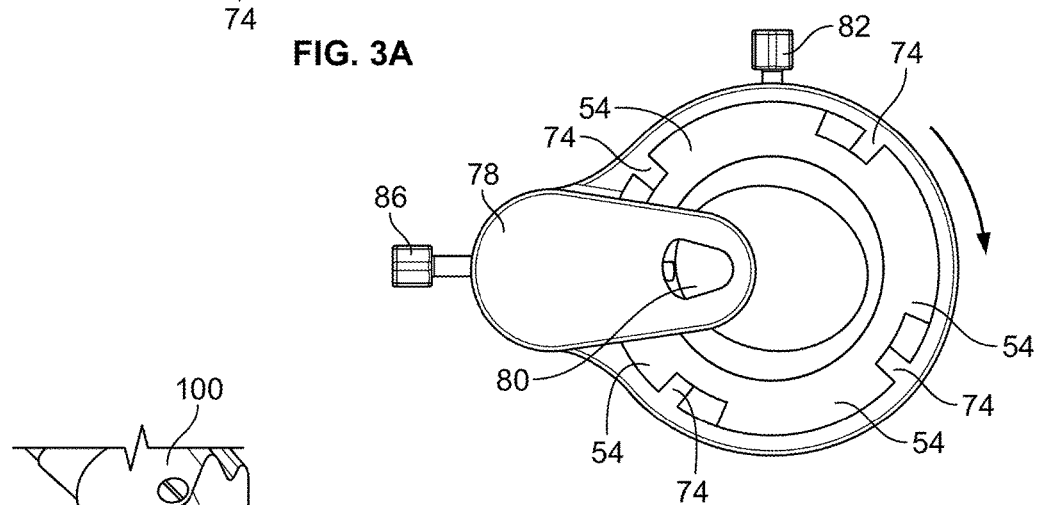

Adaptor 70 also includes a post 76 at an end of mating section 72, as shown in FIG. 2C. Post 76 extends upwards from mating section 72 to a scope holder 78 spaced apart from mating section 72. Scope holder 78 in turn extends towards a center of opening 71 defined by mating section 72 so that an aperture 80 formed through scope holder 78 is aligned with opening 71. As shown in FIGS. 3A-B, scope aperture 80 is offset from the center of opening 71 through adaptor 70, although it is contemplated that scope aperture 80 may be positioned at the center of opening 71 depending on the length of scope holder 78. Scope aperture 80, in one embodiment, is oblong so as to mate with a correspondingly-shaped section of an endoscopic viewing device 100, as described in subsequent sections.

As shown best in FIGS. 3A-B and 4C, scope adaptor 70 also includes an opening 84 extending through mating section 72 for receiving a screw or pin 82. Screw 82 may have external threads that mate with internal threads formed in opening 84 so that screw 82 can be rotated to move screw 82 into or out of opening 84 and ultimately in or out of contact with access portal 40. A knob 83 is provided on screw 82 for this purpose. Screwing screw 82 into and out of opening 84 in adaptor 70 causes adaptor 70 to be fixed or movable in relation to access portal 40, thus allowing the surgeon to fix or move the location of endoscopic viewing device 100. In particular, screwing screw 82 into opening 84 a sufficient distance causes screw 82 to bear on access portal 40 and, due to the friction between screw 82 and access portal 40, fix adaptor 70 in place. Screwing screw 82 out of opening 84 causes it to disengage with access portal 40 and allow movement of adaptor 70 about access portal 40.

FIGS. 2B and 4B depict another opening 88 formed through adaptor 70, in particular its scope holding section 78, for receiving a screw or pin 86. Opening 88, as shown in cross-section in FIG. 4B, extends through scope holder 78 and communicates with scope aperture 80. Internal threads may be formed within opening 88 to mate with external threads on screw 86 so that screw 86 can be rotated within opening 88, thereby causing movement of screw 86 into and out of opening 88. Screw 86 may include a knob 87 for facilitating its rotation. As described in more detail below, screw 86 may be screwed within opening 88 to contact endoscopic viewing device 100 and fix its location in a vertical direction, or it may be unscrewed from opening 88 to allow movement of endoscopic viewing device 100 in a vertical direction.

FIG. 2C depicts scope adaptor 70 being attached to access portal 40 via positioning mating section 72 of adaptor 70 over flange 46 of access portal 40. In particular, projections 74 of adaptor 70 are aligned with spaced-apart openings 52 through flange 46 of access portal 40 and moved through openings 52 so that projections 74 lie within channel 50 formed between flanges 46, 48. In this orientation, projections 74 and/or a bottom surface of mating section 72 of adaptor 70 may lie against a section of flange 48 so that adaptor 70 does not move axially beyond the extent of flange 48. With projections 74 arranged in channel 50 between flanges 46, 48, adaptor 70 may be rotated as shown in FIGS. 3A-B to a number of different orientations for positioning scope holder 78 circumferentially around access portal 40 and preventing movement of adaptor 70 vertically away from proximal section 44 of access portal 40. For example, as shown in FIG. 3A, adaptor 70 may be arranged in an orientation in which projections 74 are aligned with spaced-apart openings 52 (e.g., during placement of adaptor 70 onto access portal 40) and then, as shown in FIG. 3B, adaptor 70 may be rotated so that projections 74 are at least partially out of phase or not aligned with spaced-apart openings 52. In this way, projections 74 are disposed in channel 50 of access portal 40 and certain sections 54 of flange 46 that do not include spaced-apart openings 52 overlie projections 74 so that adaptor 70 is locked in an axially-fixed position (e.g., adaptor 70 cannot disengage from access portal 40 when rotated to a position such as that shown in FIG. 3B).

Adaptor 70 may be rotated three-hundred and sixty degrees (360°) about proximal section 44 of access portal 40 to position scope holder 78 around proximal section 44. In addition, scope aperture 80 is, in one embodiment, arranged offset from a center of mating section 72 of adaptor 70 (and thus off-center in relation to working channel 56 of access portal 40) so that scope aperture 80 is positioned at various eccentric positions when adaptor 70 is rotated about proximal section 44 of access portal 40. To fix adaptor 70 in a particular rotated position, a user may utilize screw 82. Screw 82, as reflected in FIG. 4C, may be screwed into opening 84 until it contacts a surface of access portal 40 arranged in channel 50 between flanges 46, 48, thus fixing adaptor 70 rotationally with respect to access portal 40 (e.g., by way of friction created between screw 82 and access portal 40). A surgeon can therefore, at his/her election, rotate adaptor 70 and fix scope holder 78 at various different locations about working channel 56 of access portal 40. If in a particular step of the surgical procedure the surgeon does not require endoscopic visualization of the working area, the surgeon can also always disengage adaptor 70 from access portal 40 by rotating it so that projections 74 are again aligned with spaced-apart openings 52, which allows the surgeon to vertically lift the adaptor 70 away from access portal 40 by moving projections 74 through openings 52.

Figure 4A:
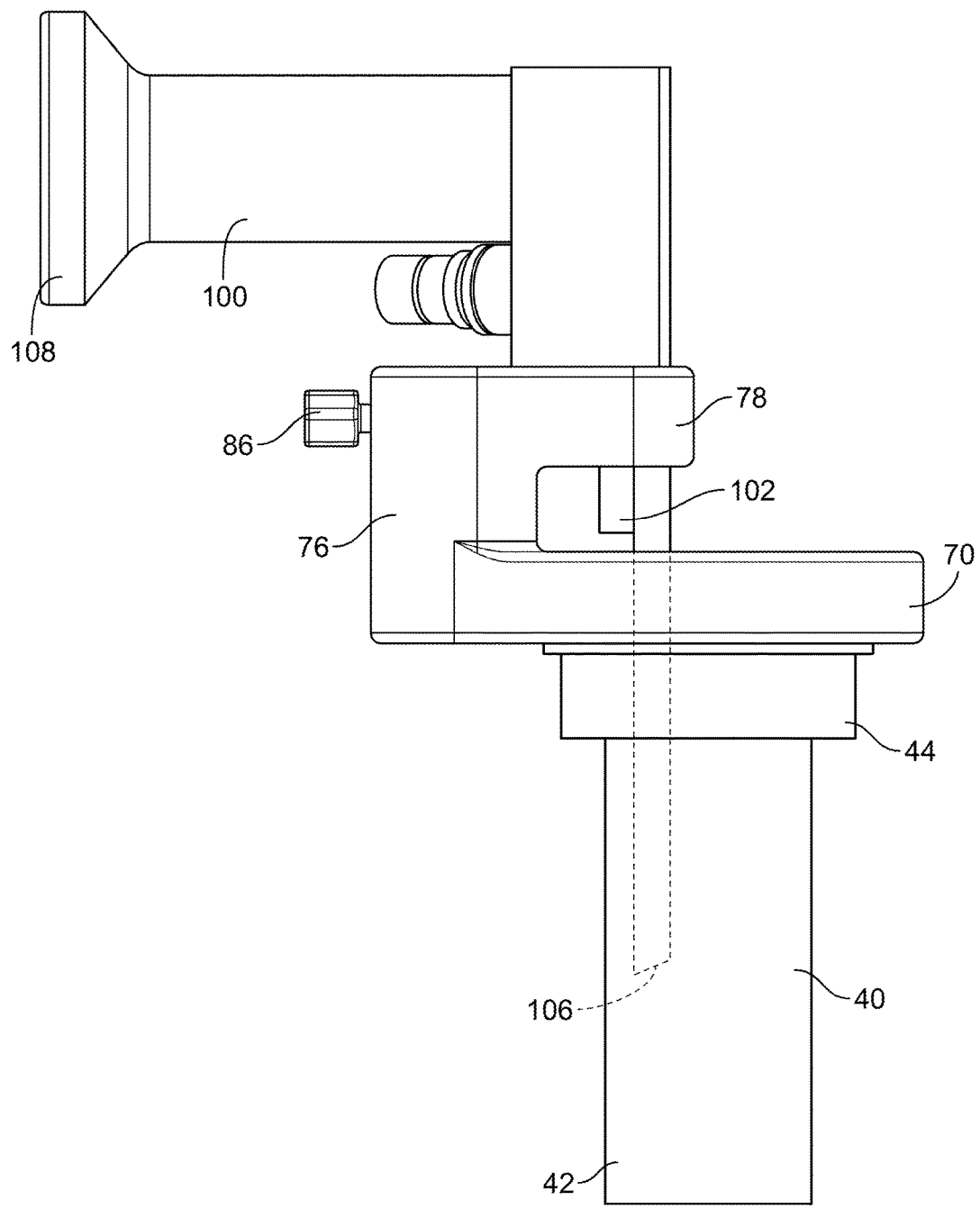
FIG. 4A is a side view of an access portal, an endoscopic viewing device, and an adaptor for holding the endoscopic viewing device, according to an embodiment of the present invention.

Referring now to FIGS. 4A-C, an endoscopic viewing device 100 is provided with access system 10. Endoscopic viewing device 100 may be any rigid or flexible/steerable endoscope known in the art at present, which is insertable into scope holder 78 of adaptor 70. Viewing device 100 includes a mounting section 102 with a geometry that matches the geometry of scope aperture 80 through scope holder 78 (e.g., an oblong geometry). In some cases, the geometries of mounting section 102 and scope aperture 80 through scope holder 78 can be selected to prevent rotation of viewing device 100 relative to adaptor 70 once mounting section 102 of viewing device 100 is situated within scope aperture 80 (as in the depicted design), but it is equally contemplated that other geometries may be used to allow rotation of viewing device 100 relative to adaptor 70 (e.g., circular or hexagonal geometries or the like that allow continuous or incremental rotation of viewing device 100 within aperture 80 of adaptor 70). Endoscopic viewing device 100 also includes an eyepiece 108 and a viewing lens 106 for viewing the working area at the surgical site. Viewing device 100 may also be connected to a monitor or other device so that the surgeon can easily see what is in the field of view of lens 106 of viewing device 100.

Referring still to FIGS. 4A-C, screw 86 extends through opening 88 in adaptor 70, in particular its post 76, to contact mounting section 102 of endoscopic viewing device 100 so that viewing device 100 may be adjusted in a vertical direction according to the surgeon's preference. Mounting section 102 of viewing device 100 is elongated so that, as it travels within scope aperture 80 of adaptor 70, mounting section 102 stays in contact with the sides of scope aperture 80 (e.g., to prevent viewing device 100 from rotating and to keep the geometries of mounting section 102 and scope aperture 80 meshed with one another). Due to its elongated nature, mounting section 102 can therefore travel axially within scope aperture 80 of adaptor 70 to move the position of lens 106 of viewing device 100 distally or proximally. Mounting section 102 can be any predetermined length to allow a particular amount of axial movement of lens 106. In addition, a portion of viewing device 100 may be of a greater dimension than scope aperture 80 of adaptor 70 so that distal movement of lens 106 past a certain point is restricted. For instance, a surface 110 on viewing device 100 may contact with adaptor 70, as shown in FIG. 4B, to prevent further distal movement of lens 106 past a predetermined point.

When the surgeon has positioned lens 106 at a desired location, screw 86 can be screwed into opening 88 in post 76 of adaptor 70 to fix mounting section 102 of viewing device 100 (and thus lens 106) at the desired position. In this manner, lens 106 may be adjusted both distally and proximally through scope aperture 80, and lens 106 may also be rotated circumferentially about access portal 40 via the movement of adaptor 70 about access portal 40, as detailed above. Thus, the surgeon is provided with a viewing device 100 that is movable to many different locations to alter the field of view for the surgeon at the working area. The operation can therefore proceed more efficiently and with better visualization of the surgical site. In addition, the surgeon can adjust the positioning of viewing device 100 vertically or circumferentially about access portal 40 so that, depending on the particular action being taken in the procedure, the best visualization of the surgical site is obtained.

A method of utilizing the aforementioned access system 10 will now be described. Access system 10 can be used in a variety of procedures, although only one (1) exemplary procedure is described. For instance, access system 10 can be utilized in virtually all surgical approaches and in all areas of the spine. In addition, it is contemplated that access portal 40, adaptor 70, and viewing device 100 can be utilized without certain aspects of access system 10 (e.g., without fixation pins 22, 24), and along a variety of different approaches. For instance, it is contemplated that access portal 40, adaptor 70, and viewing device 100 may be utilized by themselves and in surgical procedures conducted on a posterior approach (e.g., posterior lumbar interbody fusion (PLIF), transforaminal lumbar interbody fusion (TLIF), or similar procedures conducted in the cervical or other regions of the spine), surgical procedures conducted on a lateral approach, and/or surgical procedures conducted on an anterior or anterolateral approach (e.g., anterior lumbar interbody fusion or oblique lumbar interbody fusion). Put simply, access portal 40, adaptor 70, and viewing device 100 are configured for a vast variety of surgical procedures, and it is to be understood that, while only one (1) type of surgery is set forth below, others can be performed.

In one embodiment, a surgeon makes an incision in a patient's back and optionally inserts a guide wire through the incision and into contact with bone. Tissue dilators (not shown) are then inserted over the guide wire to sequentially dilate the patient's skin and tissue and atraumatically provide access to the surgical site. The tissue dilators may include tapered distal ends and internal bores that successively increase from one dilator to the next. In addition, the dilators may have different lengths, such that the dilator with the smallest internal bore has the longest length and the dilator with the largest internal bore has the shortest length.

To sequentially dilate the skin and tissue of the patient through the initial incision in the patient's back, the surgeon can insert a first dilator having a particular length and internal bore size into the incision and over the guide wire (if used), insert a second dilator having a somewhat larger internal bore and shorter length over the first dilator, and so on and so forth until an appropriate access path is established through the skin and tissue of the patient. The dilators may be inserted into the incision along a direction that intersects with an intervertebral space 20 of adjacent vertebrae 21, 25 (e.g., along a purely posterior approach, a transforaminal approach, etc.), which can be verified using standard imaging techniques, such as fluoroscopy. As a final step, the surgeon may insert access portal 40 over the last inserted dilator and then remove each of the utilized dilators out of working channel 56 of access portal 40 so that a minimally-invasive access path is established through the skin and tissue of the patient and to a position adjacent intervertebral disc space 20. Depending on the particular approach utilized (e.g., PLIF/TLIF), additional steps may be required, such as resection of vertebral bone and/or a laminectomy, to establish effective access to intervertebral disc space 20. These steps are set forth in detail in various surgical techniques published by the applicant (Stryker, Inc.) such as, for example, the publication titled "AVS™ TL Peek Spacer System: Surgical Technique," published in 2005 and provided with literature number IBATLST2B, the disclosure of which is incorporated by reference herein.

When utilizing a pedicle-based retractor, such as that shown with access system 10, the surgeon also makes separate incisions in the patient's back to allow for insertion of anchoring pins 22, 24 into bone. In particular, anchoring pins 22, 24 may be cannulated and the surgeon may make an incision in the patient's back, insert a guide wire (e.g., a K-wire) through the incision and into contact with the patient's pedicle, and then insert either pin 22, 24 over the K-wire and through the incision. This can also be done for the other pin 22, 24. With both pins 22, 24 in place and in contact with bone (e.g., the patient's pedicle), arms 30, 32 and the remainder of frame 26 of the pedicle-based retractor are attached to anchoring pins 22, 24. In addition, a clamp is attached to access portal 40 to stabilize portal 40 within the patient. In this condition, anchoring pins 22, 24 may be moved away from one another by way of sliding arm 30 along bar 34. Arm 30 may be fixed in position once it is moved to a desired location. Moving arms 30, 32 away from one another causes vertebrae 21, 25 to be distracted away from each other so that intervertebral disc space 20 is decompressed. The surgeon may then perform a variety of surgical procedures through access portal 40, such as a standard discectomy (e.g., removal of intervertebral disc material in intervertebral disc space 20) and/or a fusion procedure. A variety of surgical instruments may be inserted through working channel 56 of access portal 40, either separately or simultaneously with one another, to perform such a discectomy and/or fusion procedure; and, during the procedure, endoscopic viewing device 100 may be utilized to provide clear visualization of the working area inside the patient (e.g., intervertebral disc space 20).

Figure 3C:
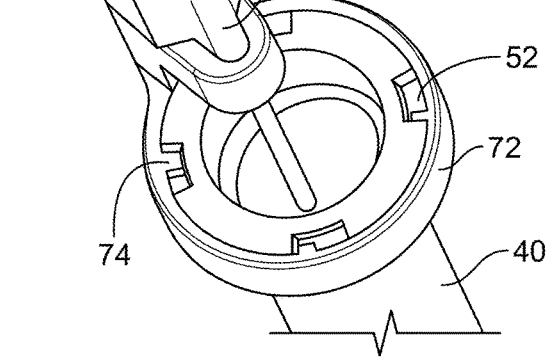
FIG. 3C is a top perspective view of an endoscopic viewing device inserted into the adaptor and access portal of FIGS. 3A-B.

With access portal 40 in place inside a patient, as set forth above, the surgeon may then attach scope adaptor 70 to access portal 40 in the manner set forth in previous sections. Indeed, as shown in FIGS. 3A-C, projections 74 of adaptor 70 are aligned with spaced-apart openings 52 through flange 46 of access portal 40, projections 74 are moved through spaced-apart openings 52, and then adaptor 70 is rotated in the manner shown in FIG. 3B to secure adaptor 70 and projections 74 within channel 50 between flanges 46, 48. The surgeon then inserts mounting section 102 of endoscopic viewing device 100 through scope aperture 80 of adaptor 70 so that the geometry of mounting section 102 mates with the geometry of scope aperture 80. In this orientation, the surgeon can selectively move viewing device 100 vertically up and down to move lens 106 vertically up and down. Lens 106 is then secured in a particular position by way of screw 86 (FIGS. 3B and 4B). And, adaptor 70 may also be rotated by the surgeon circumferentially about proximal section 44 of access portal 40, thereby causing scope holder 78 and viewing device 100 to rotate about access portal 40, at which point adaptor 70 can be secured in a rotationally-fixed position through the use of screw 82 (FIG. 4C). A surgeon is thusly provided with a variety of options for positioning viewing device 100 to gain the best visualization of the working area at the surgical site (e.g., intervertebral disc space 20).

After the surgeon performs a standard discectomy and/or other procedure under endoscopic visualization from viewing device 100, which can be adjusted in any manner to achieve clear visualization as set forth above, the surgeon may insert an interbody device into the at least partially excised disc space 20. The interbody device may be an expandable implant, such as that shown in U.S. Ser. Nos. 13/587,205 and/or 61/775,909, each of which is incorporated by reference herein, or it may be a non-expandable implant. In the case of a PLIF or TLIF procedure, an implant can be inserted unilaterally, or multiple implants may be inserted into disc space 20 to bilaterally support adjacent vertebrae 21, 25. An example of an implant(s) usable in such a procedure is discussed in the publication "AVS™ TL Peek Spacer System: Surgical Technique," incorporated by reference above. The implant or implants inserted into disc space 20 may also be packed with bone graft or other synthetic bone-growth materials to assist with achieving fusion of adjacent vertebrae 21, 25 (e.g., for alleviation of pain caused by a defect with the patient's spine). Posterior stabilization devices (e.g., rod fixation and/or other stabilizers) may also be used in connection with the insertion of such implants to stabilize the fusion procedure.

Access system 10, and in particular scope adaptor 70, access portal 40, and viewing device 100, therefore provides a system that effectively allows for improved visualization of the working area at the surgical site. The system is versatile, as set forth above, and allows the surgeon many options for altering visualization of the surgical space, and for utilizing different tools (e.g., different scopes) during the procedure.

In the devices shown in the figures, particular structures are shown as being adapted for use in an endoscopic viewing system. The invention(s) also contemplates the use of any alternative structures for such purposes, including structures having different lengths, shapes, and/or configurations. As an example, although access system 10 is in the form of a pedicle-based retraction system, other access systems may be used that do not attach to bone. For instance, access portal 40 may by itself be attached to a table arm or other supporting device to provide access through the skin and tissue of a patient (e.g., during spinal surgery), without the use of fixation pins 22, 24. Thus, while fixation pins 22, 24 are shown in connection with access system 10, such are not required and may be omitted in favor of alternate access systems that do not utilize those structures.

It is also contemplated that alternate viewing devices may be used, such as rigid endoscopes or flexible, steerable endoscopes. For instance, since viewing device 100 is only provisionally attached to adaptor 70 via screw 86, a surgeon may opt to remove viewing device 100 (which may be a rigid scope) for another viewing device that is flexible and steerable. Indeed, the surgeon may simply unscrew screw 86 and remove viewing device 100 vertically out of scope aperture 80 in exchange for another viewing device. In this scenario, the surgeon may use the flexible, steerable endoscope to, for example, visualize surgical spaces beyond the distal end of access portal 40. Since these types of endoscopes are typically pliable adjacent at least their distal end, the surgeon may visualize spaces beyond access portal 40 and navigate around body structures by manipulating the flexible portion of the scope.

As another example, although adaptor 70 is described as being used only for viewing device 100 above, adaptor 70 may include openings or mounting sections for other instrumentation, such as lighting. Indeed, an additional opening besides scope aperture 80 may be provided with adaptor 70 to allow for mounting of lighting instrumentation, which could extend into working channel 56 of access portal 40. Such lighting instrumentation could also be movable vertically as well as rotatable circumferentially about access portal 40, in a similar vein to viewing device 100. Alternatively, it is equally contemplated that other adaptors, which are substantially similar to adaptor 70, may be provided for mounting the aforementioned additional instrumentation (e.g., lighting components). To use such adaptors, adaptor 70 may merely be removed from access portal 40 in the manner set forth above, and the alternate adaptor may be attached to access portal 40 and used to support instrumentation such as lighting components, etc.

Further, while scope aperture 80 has been described as being offset from a center of working channel 56 of access portal 40, it is contemplated that scope aperture 80 (and thus viewing device 100) can be positioned at the center of working channel 56. In one embodiment, scope holder 78 may be translatable for this purpose (i.e., for moving the location of scope aperture 80 and thus viewing device 100 relative to the center of working channel 56). Stated differently, it is contemplated that scope holder 78 may be longitudinally translatable towards and/or away from the center of working channel 56 (for example, through a telescoping arrangement) so that the position of scope aperture 80, and thus viewing device 100, could be moved. In this embodiment, scope holder 78 would be fixable in position to fix the location of scope aperture 80 and viewing device 100.

Also, viewing device 100 may be rotatable within scope aperture 80, although that is not the case in the design of the figures due to the oblong shape of aperture 80 and mounting section 102 of viewing device 100. To provide a rotatable viewing device 100, mounting section 102 and scope aperture 80 may be another geometry, such as circular or hexagonal. Alternatively, mounting section 102 of viewing device 100 may simply be smaller in size than scope aperture 80, allowing rotation of viewing device 100 within aperture 80. In such an embodiment, viewing device 100 may be rotationally-fixed within aperture 80 via screw 86 or through other compressive means.

Other structures besides screw 82 may be utilized to fix adaptor 70 in position relative to access portal 40. For instance, a quick-release mechanism may be utilized. Such a mechanism might comprise an adaptor 70 that is separated or spaced apart at one section (e.g., semi-circular), allowing adaptor 70 to flex outwardly or inwardly. A connector may also be attached to opposite sections of adaptor 70 at the separation, the connector being configured to draw the opposite sections of adaptor 70 towards one another to compress adaptor 70 against access portal 40. Indeed, in some cases the connector may be a trigger that, when rotated to an orientation in which it is alongside mating section 72 of adaptor 70, causes the opposite sections of adaptor 70 to move toward one another thereby compressing adaptor 70 about access portal 40. In this way, friction between adaptor 70 and access portal 40 may fix adaptor 70 rotationally relative to access portal 40. Such a quick-release mechanism may provide an easy way for a surgeon to change the orientation of viewing device 100 and re-fix adaptor 70 relative to access portal 40 after the adjustment. Other fixation mechanisms beyond those set forth above may also be utilized, of course.

Although screw 86 is used to vertically fix viewing device 100, an alternate fixation device may be utilized, of course. As an example, a button/spring mechanism may be provided that is compressible within opening 88 to secure viewing device 100 in a desired position. In such an instance, a surface of the button, like screw 86, may contact mounting section 102 of viewing device 100 to provide compression against mounting section 102 and secure viewing device 100 vertically within scope aperture 80.

In addition, although a single screw 82, 86 is shown in the figures, it is contemplated that multiple screws 82, 86 may be utilized. This is also true of the alternate fixation structures noted immediately above (e.g., quick release mechanism and/or a compressible button).

Although the invention(s) herein has been described with reference to particular embodiments, it is to be understood that these embodiments are merely illustrative of the principles and applications of the present invention(s). It is therefore to be understood that numerous modifications may be made to the illustrative embodiments and that other arrangements may be devised without departing from the spirit and scope of the present invention(s) as defined by the appended claims.

It will also be appreciated that the various dependent claims and the features set forth therein can be combined in different ways than presented in the initial claims. It will also be appreciated that the features described in connection with individual embodiments may be shared with others of the described embodiments.

The invention claimed is:

1. A method of viewing a surgical site within a patient comprising the steps of:
    placing a working channel with a central axis and at least one opening inside the patient;
    rotating an adaptor about the central axis of the working channel such that at least one projection engages the at least one opening; and
    viewing the surgical site through a viewing device connected to the adaptor.

2. The method of claim 1, wherein the viewing device is detachably connected to a holder of the adaptor.

3. The method of claim 2, wherein the viewing device is connected to the adaptor by placing a mounting portion of the viewing device in a first aperture of the holder, wherein the holder extends proximally above a proximal end of the working channel and includes the first aperture with an axis that is aligned with the working channel, the first aperture being configured to receive the mounting portion of the viewing device.

4. The method of claim 3, wherein the step of connecting the viewing device to the holder includes the step of moving a fixation member within a second aperture of the holder to contact the viewing device and secure it in a vertical direction, the second aperture being in communication with the first aperture.

5. The method of claim 1, wherein the step of placing the working channel includes mounting the adaptor to the working channel by placing the at least one projection of the adaptor in the at least one opening of a first flange of the working channel, wherein the working channel include the first and a second flange spaced apart from one another to define a channel.

6. The method of claim 5, wherein the step of placing the working channel includes the step of moving the at least one projection of the adaptor within the channel between the first and second flanges of the working channel to rotate the adaptor about the central axis of the working channel.

7. The method of claim 6, further including the step of preventing disassociation between the adaptor and the working channel by rotating the adaptor to a first orientation wherein a portion of the first flange of the working channel overlies the at least one projection of the adaptor.

8. The method of claim 1, wherein the step of rotating the adaptor further includes the step of securing the viewing device to a desired position by securing the adaptor by a third fixation member, wherein the adaptor includes a third aperture and the third fixation member movable within the third aperture, the third fixation member being configured to move within the third aperture to rotationally fix the adaptor relative to the working channel such that the adaptor is selectively rotatable about the central axis of the working channel.

9. The method of claim 1, wherein the surgical site is a spinal site.

10. A method of viewing a surgical site within a patient comprising the steps of:
    placing an access portal inside a patient, the access portal defining a working channel;
    securing a viewing device to the access portal,
    rotating the viewing device about a central axis of the access portal to position the viewing device to view the surgical site,
    wherein the step of placing the access portal includes the step of mating an adaptor having at least one projection corresponding to at least one opening in the access portal,
    wherein the step of mating the adaptor to the access portal including the step of placing the at least one projection of the adaptor in the at least one opening of a first flange of the access portal, wherein the access portal include the first and a second flange spaced apart from one another to define a channel, and
    moving the at least one projection of the adaptor within the channel between the first and second flanges of the access portal to rotate the adaptor about the central axis of the working channel.

11. The method of claim 10, wherein the step of securing a viewing device to the access portal includes a step placing a mounting portion of the viewing device in a first aperture of a holder of the adaptor, wherein the holder extends proximally above a proximal end of the access portal and includes a first aperture with an axis that is aligned with the working channel of the access portal, the first aperture being configured to receive the mounting portion of the viewing device.

12. The method of claim 11, further including the step of rotating and securing the viewing device to a desired position by rotating the adaptor to position the viewing device to the desired position and securing the viewing device in the desired position by securing the adaptor by a third fixation member, wherein the adaptor includes a third aperture and the third fixation member movable within the third aperture, the third fixation member being configured to move within the third aperture to rotationally fix the adaptor relative to the access portal such that the adaptor is selectively rotatable about the central axis of the access portal.

13. The method of claim 10, further including the step of preventing disassociation between the adaptor and the access portal by rotating the adaptor to a first orientation wherein a portion of the first flange of the access portal overlies the at least one projection of the adaptor.

14. A method of viewing a spinal site during a surgical procedure using an access system comprising the steps of:
- dilating a patient's skin and tissue with one or more dilators to create an access path to a spinal site;
- placing an access portal of the access system over the one or more dilators, the access portal defining a working channel with a central axis and having at least one opening;
- securing a viewing device to the access portal; and
- rotating the viewing device about a central axis of the access portal to position the viewing device to view the spinal site, wherein the step of placing the access portal includes the step of mating an adaptor having at least one projection corresponding to at least one opening in the access portal, wherein the step of mating the adaptor to the access portal including the step of placing the at least one projection of the adaptor in the at least one opening of a first flange of the access portal, wherein the access portal include the first and a second flange spaced apart from one another to define a channel wherein the step of securing a viewing device to the access portal includes a step placing a mounting portion of the viewing device in a first aperture of a holder of the adaptor, wherein the holder extends proximally above a proximal end of the access portal and includes a first aperture with an axis that is aligned with the working channel of the access portal, the first aperture being configured to receive the mounting portion of the viewing device.

* * * * *